United States Patent [19]

Sakurai et al.

[11] 4,330,534

[45] May 18, 1982

[54] N[4]-ACYLCYTOSINE ARABINOSIDE COMPOSITIONS

[75] Inventors: Yoshio Sakurai, Mitaka; Tateshi Kataoka, Tokyo; Fujiko Oh-hashi, Kounosu, all of Japan

[73] Assignee: Asahi Kasei Kogyo Kabushiki Kaisha, Japan

[21] Appl. No.: 169,422

[22] Filed: Jul. 16, 1980

[30] Foreign Application Priority Data

Aug. 2, 1979 [JP] Japan .................................. 54/98075

[51] Int. Cl.[3] ...................... A61K 31/70; C07H 19/08; A61K 31/705
[52] U.S. Cl. .................................... 424/182; 424/180; 536/23
[58] Field of Search .................... 424/180, 182; 536/23

[56] References Cited

U.S. PATENT DOCUMENTS 3,991,045  11/1976  Ishida et al. .......................... 536/23
4,055,716  10/1977  Ishida et al. .......................... 536/23

FOREIGN PATENT DOCUMENTS 52-114015 of 1977 Japan .................................. 424/180

OTHER PUBLICATIONS

Rahman et al., "Chem. Abst.", vol. 89, 1978, P 94,958f.
Aoshima et al., "Cancer Research", vol. 36, pp. 2726-2732, Aug. 1976.
Aoshima et al., "Cancer Research", vol. 37, pp. 2481-2486, Aug. 1977.
Juliano et al., "Biochemical Pharmacology", vol. 27, pp. 21-27, 1978.

*Primary Examiner*—Johnnie R. Brown
*Attorney, Agent, or Firm*—Finnegan, Henderson, Farabow, Garrett & Dunner

[57] ABSTRACT

A N[4]-acylcytosine arabinoside preparation which consists essentially of (a) a liposome of lecithin and (b) a N[4]-acylcytosine arabinoside having a $C_{6-18}$ aliphatic acyl group and being encapsulated in the liposome.

3 Claims, No Drawings

$N^4$-ACYLCYTOSINE ARABINOSIDE COMPOSITIONS

BACKGROUND OF THE INVENTION

1. Field of the Invention

This invention relates to $N^4$-acylcytosine arabinoside preparation having an enhanced activity as anti-tumor agents.

2. Description of the Prior Art $N^4$-acylcytosine arabinoside is a derivative of cytosine arabinoside which is known as an agent for an acute leukemia, and it is particularly useful for anti-tumor agents having an improved durability of the activity and resistance to cytidine deaminase while it maintains a superior anti-tumor activity of cytosine arabinoside. (Cancer Research, Vol. 36, Page 2726 and Vol. 37, Page 2481)

The inventors of this invention have found that the anti-tumor activity of cytosine arabinoside is drastically enhanced by encapsulating cytosine arabinoside into liposomes comprising lipids such as sphingomyelin and lecithin. They have also found that an additive such as stearylamine and dicetyl phosphate was required to add cytosine arabinoside, since the amount of cytosine arabinoside encapsulated in liposomes is considerably small compared with that employed as the starting material. (Japanese Patent Application (OPI) 114015/1977) The above described additive, however, is harmful to living body. Therefore, it has been an important subject to increase the encapsulating efficiency of cytosine arabinoside into liposomes without using any harmful additive in this field.

The object of this invention is to provide a $N^4$-acylcytosine arabinoside preparations having an enhanced anti-tumor activity.

Another object of this invention is to provide an encapsulated $N^4$-acylcytosine arabinoside preparation without using any harmful additives.

SUMMARY OF THE INVENTION

These objects are realized in accordance with this invention pursuant to which there is provided a preparation which consists essentially of a liposome of lecithin and a $N^4$-acylcytosine arabinoside having a $C_{6-18}$ aliphatic acyl group.

DETAILED DESCRIPTION OF THE INVENTION

The liposome which can be used in this invention is lecithin, and especially egg yolk lecithin. One constituent element of lecithin such as distearoyl phosphatidyl choline, dipalmitoyl phosphatidyl choline, dimyristoyl phosphatidyl choline and dioleoyl phosphatidyl choline or a mixture thereof can also be used. When the fluidity of a liposome film must be improved, cholesterol can be added by the conventional method.

Exemplary $N^4$-acylcytosine arabinosides which can be employed in this invention include $N^4$-acylcytosine arabinosides containing an aliphatic group having 6 to 18 carbon atoms such as $N^4$-caproylcytosine arabinoside, $N^4$-caprylylcytosine arabinoside, $N^4$-caprilcytosine arabinoside, $N^4$-lauroylcytosine arabinoside, $N^4$-myristoylcytosine arabinoside, $N^4$-palmitoylcytosine arabinoside and $N^4$-stearoylcytosine arabinoside. If the aliphatic groups having less than 6 carbon atoms or more than 18 carbon atoms are employed, activity of agents does not increase appreciably from the viewpoint of statistical significance.

The preparations of this invention can be prepared by the following method.

Lecithin, $N^4$-acylcytosine arabinoside and if necessary, cholesterol are dissolved in an appropriate organic solvent, respectively, and then the solution were well mixed together. The mixed solution is dried in a flask under reduced pressure to make a thin film on the inner wall of the flask. After water is added in the flask, the flask is shaken mechanically until the film is peeled from the inner wall. The suspension of the preparation of this invention can be obtained by the above described method. The preparation can be isolated by centrifuging the suspension.

The preparations of this invention can be administered in various manners by modifying or not modifying the preparations. For example, the preparations of this invention can be used for oral, intraperitoneal, intravenous or subcutaneous administrations and the like by suspending the preparations in water or physiological sodium chloride solution.

The following Examples are given to illustrate the present invention more specifically. However, it should be understood that the invention is in no way limited by these Examples.

EXAMPLE 1

In 1 ml, 2 ml and 0.4 ml of a 2:1 by volume mixed solvent of chloroform and methanol were dissolved 40 μmole of egg yolk lecithin, 30 μmole of cholesterol and 8 μmole of $N^4$-acylcytosine arabinoside (hereinafter referred to as "ACA"), respectively. Each of the solutions was placed together in 100 ml of a heat-shaped flask and well mixed. Then the flask was rotated in a water bath at a temperature of 40° C. to remove the solvent under reduced pressure, resulting in a thin film on the inner wall of the flask. After the flask was dried in a desiccator under vacuum for 3 hours, two 6×9 mm spatulafuls of glass beads having a diameter of 0.18 mm and 4 ml of physiological sodium chloride solution were added into the flask. Then the flask was shaken by a test tube vibrator until the film on the inner wall of the flask was peeled. The glass beads were removed from thus obtained suspension and the anti-tumor activity of the suspension was tested according to the following experiment.

$CDF_1$ mice which had been inoculated intraperitoneally with $10^5$ of L-1210 leukemic cells, each group consisting of 8 animals, were given intraperitoneal injection of the above described suspension containing 10–20 μmole/kg of ACA on the first and the fifth day from the transplant day. The activity was measured by the value (T/C)×100 wherein T is the average survival day of injected test mice groups and C is the average survival day of non-injected comparative mice groups.

A comparative experiment was conducted by repeating the above described experiment using an ACA suspension containing ACA and a physiological sodium chloride solution containing 0.5% of TWEEN 80 (trade name for polyoxyethylene sorbitan monooleate manufactured by Kao Atlas Co., Ltd., Japan). The results are shown in Table 1.

TABLE 1

| Acyl Group in ACA | Amount of Injection (μmole/Kg) | T/C (%) (a) Liposome-Encapsulated ACA | (b) ACA Suspension | Statistical Significance between (a) and (c) |
| --- | --- | --- | --- | --- |
| $N^4$-butyryl | 20 | 104 | 101 | X |
| $N^4$-caproyl | 20 | 110 | 103 | O |
| $N^4$-caprylyl | 20 | 115 | 108 | O |
| $N^4$-capryl | 20 | 136 | 114 | O |
| $N^4$-lauroyl | 20 | 128 | 112 | O |
| $N^4$-myristoyl | 20 | 181 | 118 | O |
| $N^4$-palmitoyl | 20 | 164 | 131 | O |
| $N^4$-stearoyl | 10 | 164 | 139 | O |
| $N^4$-arachidoyl | 10 | 143 | 135 | X |

Note:
O shows that the difference between (a) and (b) has statistical significance, and X shows that the difference has no statistical significance.

EXAMPLE 2

The anti-tumor activity measured by the same method as Example 1 using the following preparations prepared by the same manner as Example 1 except
(A) using $N^4$-myristoylcytosine arabinoside as ACA or
(B) using $N^4$-myristoylcytosine arabinoside as ACA and without using cholesterol or
(C) using the following comparative preparation prepared by dispersing $N^4$-myristoylcytosine arabinoside and liposome consisting of lecithin and cholesterol into a physiological sodium chloride solution containing 0.5% of TWEEN 80 and mixing. The amount of injection was 20 μmole/Kg. The results are shown in Table 2.

TABLE 2

| Preparations | T/C (%) |
| --- | --- |
| (A) | 165 |
| (B) | 200 |
| (C) | 122 |

As is clear seen from Table 2, the difference between (A) and (C), or (B) and (C) has statistical significance.

EXAMPLE 3

Example 1 was repeated except using $N^4$-myristoylcytosine arabinoside as ACA, without using cholesterol, and using various phosphatidyl cholines in place of lecithin. An amount of injection was 20 μmole/Kg. The results are shown in Table 3.

TABLE 3

| Diacyl Group of Phosphatidyl Choline | T/C (%) |
| --- | --- |
| Distearoyl | 156 |
| Dipalmitoyl | 162 |
| Dimyristoyl | 165 |
| Dioleoyl | 148 |

EXAMPLE 4

The ACA incorporation rate into liposome was measured by the following experiment.

In 0.25 ml, 0.5 ml, 0.1 ml and 0.25 ml of a 2:1 by volume mixed solvent of chloroform and methanol were dissolved 10 μmole of egg yolk lecithin, 7.5 μmole of cholesterol, 2 μmole of $N^4$-myristoylcytosine arabinoside and, if necessary, 1 μmole of stearylamine, respectively. Each of the solutions was placed together in 100 ml of a heart-shaped flask and well mixed. Then the flask was rotated in a water bath at a temperature of 40° C. to remove the solvent under reduced pressure, resulting in a thin film on the inner wall of the flask. After the flask was dried in a desiccator under vacuum for 3 hours, two 6×9 mm spatulafuls of glass beads having a diameter of 0.18 mm and 2 ml of physiological sodium chloride solution were added into the flask. The flask was shaken by a test tube vibrator until the film on the inner wall of the flask was peeled.

All the contents of the flask was poured into 40 ml of a polyethylene test tube for a centrifuge. The residue in the flask was washed three times, each with 10 ml of a physiological sodium chloride solution and the washing liquid was all collected and added into the above described test tube. The glass beads were removed and the test tube was centrifuged with a load of 13,000 g for 15 minutes at 4° C. After the upper liquid layer was removed and 30 ml of a fresh physiological sodium chloride solution were added in the test tube and well mixed, the test tube was centrifuged. This operation was repeated two more times, and discarding upper liquid layer to give liposome. The liposome thus obtained was dried and the ACA incorporation rate into the liposome was measured.

The amount of liposome recoveries was calculated from the amount of organic phosphorus contained in the liposome.

The amount of $N^4$-myristoylcytosine arabinoside recoveries was calculated by measuring the absorbance of the liposome in chloroform at 300 nm. The results are shown in Table 4.

TABLE 4

| Liposome | Recovery Rate of Liposome (%) | Recovery Rate of ACA (%) | Incorporation Rate of ACA (%) |
| --- | --- | --- | --- |
| Lecithin/Cholesterol/Stearylamine | 56 | 43 | 77 |
| Lecithin/Cholesterol | 81 | 70 | 86 |

For the comparison, a preparation using cytosine arabinoside was prepared by the following procedure, and the cytosine arabinoside incorporation rate into liposome was measured.

In 0.25 ml, 0.5 ml and 0.25 ml of a 2:1 by volume mixed solvent of chloroform and methanol were dissolved 10 μmole of egg yolk lecithin, 7.5 μmole of cholesterol and, if necessary, 1 μmole of stearylamine, respectively. Each of the solutions was placed together in 100 ml of a heart-shaped flask and well mixed. Then the flask was rotated in a water bath at a temperature of 40° C. to remove the solvent under reduced pressure, resulting in a thin film on the inner wall of the flask. After the flask was dried in a desiccator under vacuum for 3 hours, two 6×9 mm of spatulafuls of glass beads having a diameter of 0.18 mm and 1 ml of cytosine arabinoside solution (300 μmole/ml) were added into the flask. The flask was shaken by a test tube vibrator until the film on the inner wall of the flask was peeled.

All the contents of the flask were poured into 40 ml of a polyethylene test tube for centrifuge. The residue in the flask was washed three times, each with 10 ml of a physiological sodium chloride solution and the washing liquid was all collected and added into the above described test tube. The glass beads were removed and the test tube was centrifuged with a load of 13,000 g for 15 minutes at 4° C. After the upper liquid layer was removed and 30 ml of a fresh physiological sodium chloride solution were added in the test tube and well mixed, the test tube was further centrifuged. This operation was repeated two more times, and discarding upper liquid layer to give liposome. The liposome thus obtained was dried and the cytosine arabinoside incorporation rate into the liposome was measured.

The amount of liposome recoveries was calculated by the same manner as the Experiment described above. The amount of cytosine arabinoside recoveries was calculated by measuring the absorbance of the liposome in chloroform at 280 nm. The results are shown in Table 5.

TABLE 5

| Liposome | Recovery Rate of Liposome (%) | Recovery Rate of Cytosine Arabinoside (%) | Incorporation Rate of Cytosine Arabinoside (%) |
| --- | --- | --- | --- |
| Lecithin/Cholesterol /Stearylamine | 70 | 4.8 | 6.9 |
| Lecithin/Cholesterol | 87 | 2.0 | 2.3 |

While the invention has been described in detail and with reference to specific embodiments thereof, it will be apparent to one skilled in the art that various changes and modifications can be made therein without departing from the spirit and scope thereof.

What is claimed is:

1. A $N^4$-acylcytosine arabinoside composition which consists essentially of (a) a liposome of lecithin and (b) a $N^4$-acylcytosine arabinoside having a $C_{6-18}$ aliphatic acyl group encapsulated in the liposome, said composition containing no substantial amount of stearylamine or dicetyl phosphate.

2. The $N^4$-acylcytosine arabinoside composition of claim 1, wherein the liposome of lecithin contains cholesterol.

3. The $N^4$-acylcytosine arabinoside composition of claim 1, wherein the aliphatic acyl group is selected from the group of caproyl, caprylyl, capryl, lauroyl, myristoyl, palmitoyl and stearoyl.

* * * * *